(12) United States Patent
Muntendam

(10) Patent No.: US 11,246,851 B2
(45) Date of Patent: Feb. 15, 2022

(54) PHARMACEUTICAL COMPOSITIONS OF FUROSEMIDE AND USES THEREOF

(71) Applicant: SQ Innovation AG, Zug (CH)

(72) Inventor: Pieter Muntendam, Boxford, MA (US)

(73) Assignee: SQ Innovation AG, Zug (CH)

( * ) Notice: Subject to any disclaimer, the term of this patent is extended or adjusted under 35 U.S.C. 154(b) by 0 days.

(21) Appl. No.: 16/733,359

(22) Filed: Jan. 3, 2020

(65) Prior Publication Data
US 2020/0215020 A1    Jul. 9, 2020

Related U.S. Application Data

(60) Provisional application No. 62/788,244, filed on Jan. 4, 2019.

(51) Int. Cl.
*A61K 31/341*    (2006.01)
*A61K 47/40*    (2006.01)

(52) U.S. Cl.
CPC ............ *A61K 31/341* (2013.01); *A61K 47/40* (2013.01)

(58) Field of Classification Search
None
See application file for complete search history.

(56) References Cited

U.S. PATENT DOCUMENTS

| | | | |
|---|---|---|---|
| 4,663,348 A | 5/1987 | Chafetz et al. | |
| 4,698,361 A | 10/1987 | Di Schiena | |
| 5,134,127 A | 7/1992 | Stella et al. | |
| 5,376,645 A | 12/1994 | Stella et al. | |
| 5,633,240 A | 5/1997 | Ranade | |
| 5,814,623 A | 9/1998 | Ranade | |
| 8,241,661 B1 | 8/2012 | Fuisz et al. | |
| 8,282,366 B2 | 10/2012 | Hilber et al. | |
| 8,372,809 B2 | 2/2013 | Unemori et al. | |
| 8,414,532 B2 | 4/2013 | Brandt et al. | |
| 9,884,039 B2 | 2/2018 | Michaels et al. | |
| 10,272,064 B2 | 4/2019 | Michaels et al. | |
| 10,391,105 B2 | 8/2019 | Cashman et al. | |
| 2008/0076828 A1 | 3/2008 | Dalton et al. | |
| 2009/0233951 A1 | 9/2009 | Somberg et al. | |
| 2011/0060280 A1 | 3/2011 | Caffey et al. | |
| 2012/0077829 A1 | 3/2012 | Somberg et al. | |
| 2013/0252932 A1 | 9/2013 | Seward | |
| 2016/0051507 A1 | 2/2016 | Michaels et al. | |
| 2018/0303790 A1 | 10/2018 | Michaels et al. | |
| 2020/0038364 A1 | 2/2020 | Michaels et al. | |

FOREIGN PATENT DOCUMENTS

| | | |
|---|---|---|
| CA | 2685331 C | 7/2016 |
| EP | 0801950 A1 | 6/1983 |
| EP | 1078636 A1 | 2/2001 |
| WO | WO-1992021769 A1 | 12/1992 |
| WO | WO-1996006615 A1 | 3/1996 |
| WO | WO-2002038186 A1 | 5/2002 |
| WO | WO-2009140659 A1 | 11/2009 |
| WO | WO-2010030667 A1 | 3/2010 |
| WO | WO-2014165660 A1 | 10/2014 |

OTHER PUBLICATIONS

Rowe, R.C., Sheskey, P.J. and Quinn, M.E. (2009) Handbook of Pharmaceutical Excipients. 6th Edition, Pharmaceutical Press, p. 210-214.*
Ammar et al., "Inclusion complexation of furosemide in cyclodextrins: Part 1. Effect of cyclodextrins on the physicochemical characteristics of furosemide," *Pharmazie*, vol. 54, pp. 142-144 (1999).
Captisol Safety Data Sheet, dated Feb. 4, 2016, 2 pages.
El-Shenawy et al., "Enhancement of Solubility and Dissolution Rate of Torsemide as Poorly Soluble Loop Diuretic by Inclusion Complexation with both β-Cyclodextrin and Hydroxypropyl-β-Cyclodextrin," *Ijppr.Human*, vol. 7, pp. 221-235 (2016).
Garnero et al., "Improving furosemide polymorphs properties through supramolecular complexes of β-cyclodextrin," *Journal of Pharmaceutical and Biomedical Analysis*, vol. 95, pp. 139-145 (2014).
International Search Report and Written Opinion of the International Searching Authority, the European Patent Office, for International Application No. PCT/EP2019/084446, dated Mar. 17, 2020, 10 pages.
International Search Report and Written Opinion of the International Searching Authority, the European Patent Office, for International Application No. PCT/EP2020/050098, dated Mar. 25, 2020, 13 pages.
Jain et al., "Sulfobutyl Ether$_7$ β-Cyclodextrin (SBE$_7$ β-CD) Carbamazepine Complex: Preparation, Characterization, Molecular Modeling, and Evaluation of In Vivo Anti-epileptic Activity," *AAPS PharmSciTech*, vol. 12, pp. 1163-1175, (2011).
Ozdemir & Ordu, "Improvement of dissolution properties of furosemide by complexation with beta-cyclodextrin," *Drug Dev Ind Pharm*, vol. 24(1), pp. 19-25, (1998). (Abstract only).
Press release entitled "Ligand and SQ Innovation Enter Into Exclusive Worldwide Captisol® License and Supply Agreements for High-Concentration Furosemide Formulation," dated Jul. 8, 2019, 5 pages.
Santos et al., "Stability of furosemide and aminophylline in parenteral solutions," *Brazilian Journal of Pharmaceutical Sciences*, vol. 47, pp. 89-96 (2011).
Sica et al., "Subcutaneous Furosemide in Heart Failure," *JACC: Basic to Translational Science*, vol. 3, pp. 25-34 (2018).
Spamer et al., "Characterization of the complexes of furosemide with 2-hydroxypropyl-β-cyclodextrin and sulfobutyl ether-7-β-cyclodextrin," *European Journal of Pharmaceutical Sciences*, vol. 16, pp. 247-253 (2002).

* cited by examiner

*Primary Examiner* — Po-Chih Chen
(74) *Attorney, Agent, or Firm* — Dechert LLP

(57) ABSTRACT

A pharmaceutical composition and a method of administering the pharmaceutical composition to a patient suffering from edema, heart failure, kidney or liver disease or having symptoms thereof are disclosed. The pharmaceutical composition includes furosemide, or a pharmaceutically acceptable salt, hydrate or ester thereof and a cyclodextrin.

28 Claims, 1 Drawing Sheet

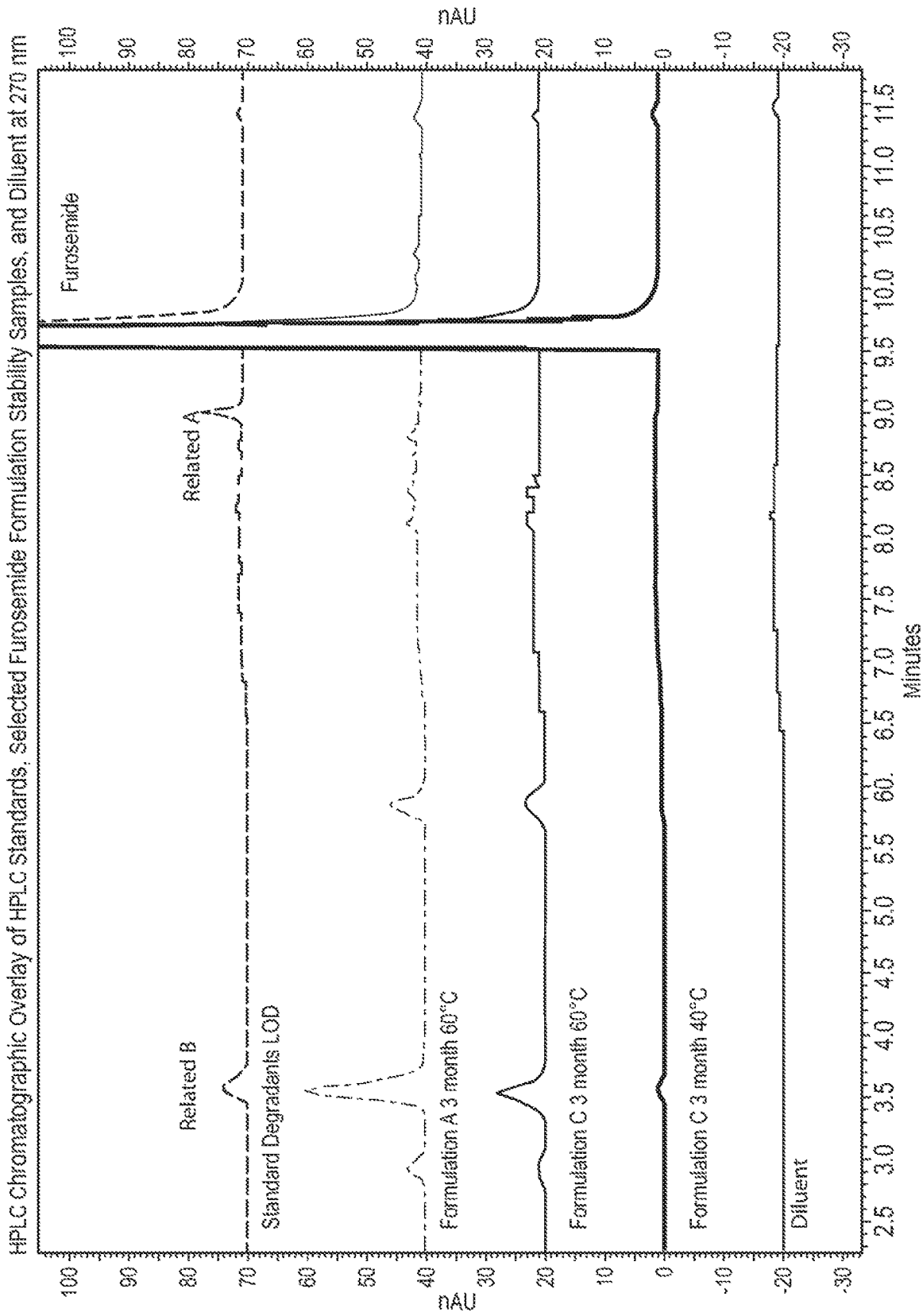

PHARMACEUTICAL COMPOSITIONS OF FUROSEMIDE AND USES THEREOF

CROSS-REFERENCE TO RELATED APPLICATIONS

This application claims the benefit of and priority to U.S. Provisional Patent Application Ser. No. 62/788,244, filed Jan. 4, 2019; the contents of which are hereby incorporated by reference in their entirety.

FIELD OF THE INVENTION

The present disclosure relates to pharmaceutical compositions containing furosemide and a cyclodextrin and methods of administering the pharmaceutical compositions to a patient. More specifically, the present disclosure relates to pharmaceutical compositions containing furosemide and a cyclodextrin and uses thereof.

BACKGROUND

Furosemide is a benzoic-sulfonamide-furan used as a potent loop diuretic with fast onset and short duration for the treatment of hypertension, edema and edema related conditions, such as congestive heart failure, cirrhosis of the liver or liver failure, and other renal diseases. Furosemide is typically administered orally for chronic treatment. Under certain circumstances furosemide is administered parenterally to patients with decompensated heart failure or other forms of advanced edema. Parenteral administration is typically done by intravenous bolus administration of infusion.

Furosemide is poorly soluble. A typical injectable formulation is alkaline and contains 8-10 mg of furosemide per mL requiring 8-10 mL to administer a typical clinical dose of 80 mg. Increasing the concentration of furosemide to reduce the volume of administration may cause precipitation, impacts the stability of a pharmaceutical formulation and presents additional challenges. Reducing the pH may also cause precipitation.

Furthermore, certain clinical uses are precluded or restricted by a high pH in a pharmaceutical formulation, including subcutaneous administration and use in certain infusion fluids or infusion systems where precipitation may occur.

Therefore, to provide a therapeutic dose of furosemide to a patient by subcutaneous injection or small volume infusion, it is necessary for a pharmaceutical composition of furosemide to have higher solubility at physiological pH to reduce drug irritation and effective drug delivery with minimal or negligible adverse toxicological effects.

Additionally, a furosemide formulation that is stable and suitable for administration at neutral pH may be combined with other medications for intravenous administration. This may facilitate use of furosemide in certain circumstances such as in the critical care setting or in neonatal or pediatric use.

Thus, a need exists for therapeutically effective improved pharmaceutical compositions containing furosemide at physiological pH.

SUMMARY

The present disclosure provides a pharmaceutical composition containing furosemide or a pharmaceutically acceptable form of the furosemide and a cyclodextrin, or cyclodextrin derivatives. The present disclosure also provides a method of treating a patient suffering from edema, heart failure, kidney or liver disease or having symptoms thereof by administering the pharmaceutical composition containing the furosemide or any such pharmaceutical form of the furosemide and the cyclodextrin or the cyclodextrin derivatives.

In one aspect, the present disclosure provides the pharmaceutical composition including the furosemide or a pharmaceutically acceptable salt, hydrate or ester of the furosemide and the cyclodextrin. In an embodiment, the cyclodextrin is a β-cyclodextrin. The β-cyclodextrin present in the pharmaceutical composition is a sulfobutyl ether derivative of β-cyclodextrin. In another embodiment of the present disclosure, the pharmaceutical composition includes the furosemide and the sulfobutyl ether derivative of β-cyclodextrin. In certain embodiments, the sulfobutyl ether derivative of β-cyclodextrin is captisol.

The present disclosure also provides the pharmaceutical composition including the furosemide or derivatives thereof and a cyclodextrin or cyclodextrin derivatives for administration at a pH value from about 7.0 and about 8.5. In an embodiment, the present disclosure provides the pharmaceutical composition including the furosemide or a pharmaceutically acceptable salt, hydrate or ester thereof, and the cyclodextrin at an amount of less than or equal to 50% of the pharmaceutical composition. The pharmaceutical composition contains the furosemide from about 8 mg/mL and 30 mg/mL. The pH value of the pharmaceutical composition is from about 7.0 and about 8.7. In certain embodiments, the pH value of the pharmaceutical composition is from about 7.2 to about 7.6.

In another aspect, the present disclosure provides a method of treating a patient suffering from edema, heart failure, kidney or liver disease or having symptoms thereof. The method includes administering to the patient a therapeutically effective amount of a pharmaceutical composition containing furosemide, or a pharmaceutically acceptable salt, hydrate or ester thereof and a cyclodextrin. In some embodiments, the method includes administering from 20 and 200 mg of the furosemide. In certain embodiments, the amount of the cyclodextrin is less than or equal to 50% of the pharmaceutical composition. In various embodiments, the method includes administering the pharmaceutical composition at a pH value from about 7.0 and about 8.5. In some embodiments, the method includes administering the pharmaceutical composition at the pH value from about 7.2 and about 7.6.

In some embodiments, the present disclosure provides the pharmaceutical composition for subcutaneous administration and intravenous administration. The method further includes administering a therapeutically effective dose of the pharmaceutical composition to the patient using a pump device. The pump device is a patch device for parenteral administration of the composition. In another embodiment, the pharmaceutical composition is administered to the patient using an injection device. The injection device is an auto injector device. In various embodiments, the pharmaceutical composition is administered to the patient subcutaneously or intravenously using the patch device or the auto injector device.

The foregoing as well as other features and advantages of the present disclosure will be more fully understood from the following description, examples, and claims.

BRIEF DESCRIPTION OF THE DRAWINGS

The drawing described below is for illustration purpose only and is not intended to limit the scope of the present disclosure in any way.

FIG. 1 is a HPLC chromatographic overlay of HPLC standards, selected furosemide formulation stability samples, and diluent.

DETAILED DESCRIPTION

The present disclosure demonstrated in this application includes mere illustrations of the invention. A skilled artisan will appreciate that various alternate embodiments and forms may be prepared. Examples, therefore, given are only for illustration purposes without any intention to restrict the embodiments to a given set of examples. Specific functional aspects are provided merely to enable a skilled artisan to perform the invention and should not be construed as limitations of the invention.

The use of the terms "include," "includes," "including," "have," "has," "having," "comprise," "comprises," "comprising" or the like should be generally understood as open-ended and non-limiting unless specifically stated otherwise.

The present disclosure includes pharmaceutical compositions of furosemide and a cyclodextrin and methods of administering the pharmaceutical compositions for treating a patient suffering from edema, heart failure, kidney or liver disease or having such disease symptoms. More specifically, the present disclosure provides the pharmaceutical compositions having the furosemide and a β-cyclodextrin or a derivative of β-cyclodextrin such as a sulfobutyl ether derivative. In certain embodiments, the sulfobutyl ether derivative of β-cyclodextrin is captisol. The cyclodextrin can be at an amount of less than or equal to 50% of the pharmaceutical composition at a pH value from about 7.0 to about 8.7. The pharmaceutical composition is suitable for parenteral administration, more specifically, suitable for subcutaneous and intravenous administration. The pharmaceutical compositions are useful in the treatment of edema, hypertension or heart failure in a patient having or exhibiting symptoms of such conditions.

As used herein, "furosemide" refers to a compound having the formula $C_{12}H_{10}ClN_2O_5S$ or $C_{12}H_{11}ClN_2O_5S$ and pharmaceutically acceptable salts, hydrates and esters thereof, for example, furosemide sodium salt ($C_{12}H_{10}ClN_2NaO_5S$) and furosemide quaternary ammonium salts or any of the amino acid salts including basic amino acids of natural origin such as ornithine, lysine and arginine, which shall include L-arginine, DL-arginine, L-lysine, DL-lysine, L-ornithine, DL-ornithine, or histidine and any variations thereof. Furosemide can be referred to by other names, such as frusemide, 5-(aminosuiphonyl)-4-chloro-2-[(2-furanyi-methyl) amino] benzoic acid, or its IUPAC name, 4-chloro-2-(furan-2-ylmethylamino)-5-sulfamoylbenzoic acid, or its common trade names, such as Lasix, Furosemid and Furanthril. It is understood that "furosemide" will further refer to any precursor or metabolite, such as 4-chloro-N-furyl-5-sulfamoyl-anthranylic acid as may be required for administration.

As used herein, "cyclodextrin" refers to cyclic compounds of 5 or more α-D-glucopyranoside units linked by 1, 4 glycosidic bonds, or compounds containing glucose monomers ranging from six to eight units in a ring designated as 6 glucose subunits known as α-cyclodextrin, 7 glucose subunits known as β-cyclodextrin and with 8 glucose subunits known as γ-cyclodextrin. In addition, the present disclosure includes cyclodextrin-related compounds, for example, compounds derived from cyclodextrins or structurally-related to cyclodextrins.

As used herein, "CAPTISOL®" refers to the trade name for a proprietary modified mixture of cyclodextrin preparation with a modified structure to optimize the solubility and stability of drugs. CAPTISOL® is a mixture of polyanionic β-cyclodextrin derivatives of a sodium sulfonate salt tethered to the lipophilic cavity of a butyl ether group, or sulfobutyl ether. CAPTISOL® is commercially available from Ligand Pharmaceuticals Inc. located in San Diego, Calif.

As used herein, the term "captisol" is a mixture of polyanionic β-cyclodextrin derivatives of a sodium sulfonate salt separated from the hydrophobic cavity of the β-cyclodextrin with a butyl ether spacer group. Chemically, captisol is also referred to as sulfobutyl ether beta-cyclodextrin sodium.

As used herein, "derivative" refers to a modified form of a compound generated by various methods or processes including, but not limited to, methylation, acetylation, substitutions such as alkylation, amidation, quaternization, thiolation, sulfation, and oxidation, chain elongations such as cross-linking and grafting, and depolymerization by chemical, physical, or biological including enzymatic means. The methods and processes can be employed either alone or in any combination without any specific order.

As used herein, "preventing or treating" refers to partially or completely alleviating and/or ameliorating the condition and/or symptoms thereof, and/or preventing its re-occurrence or halting its progression. The present disclosure accordingly includes a method of providing to the patient a combination product that includes a compound or therapeutic composition of the present disclosure in combination or association with a pharmaceutically acceptable carrier, solubilizer or an appropriate buffer.

As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

As used herein, "therapeutically effective" refers to a substance or an amount that elicits a desirable biological activity or effect reducing or arresting disease processes. For example, a "therapeutically effective amount" of a composition can deliver a dose (also referred to as a "therapeutic dose") sufficient to elicit the desired biological response. In the present invention, the desired biological response is "treating" of edema, heart failure, kidney or liver disease or having symptoms thereof. As used herein, "treating" refers to partially or completely alleviating and/or ameliorating the condition and/or symptoms thereof.

As used herein, "administration" refers to parenteral including intravenous, subcutaneous, topical, transdermal, intradermal, transmucosal, intraperitoneal, intramuscular, intracapsular, intraorbital, intracardiac, transtracheal, subcuticular, intraarticular, subcapsular, subarachnoid, intraspinal, epidural and intrasternal injection and infusion, unless specifically mentioned. Specifically, the pharmaceutical composition of the present disclosure can be administered parenterally including infusion, injection or implantation, which includes subcutaneous and intravenous administration. When administered for the treatment of a disease state or disorder, it is understood that an effective dosage can vary depending upon many factors such as the compound or therapeutic composition utilized, the mode of administration, and severity of the condition being treated, as well as the various physical factors related to the individual being treated. In therapeutic applications, a compound or therapeutic composition of the present disclosure can be provided to a patient already suffering from a disease, for example, edema related disorders, in an amount sufficient to at least partially ameliorate the symptoms of the disease and its complications and halt or slow down the disease progression. If administered to a patient suffering from the condition prior to clinical manifestation, the administration of a therapeutic composition may prevent the first clinical manifestation or delay its onset.

As used herein, "patient" refers to a mammal, such as a human or a domesticated animal such as a pet or livestock.

As used herein, the term "about" refers to a ±10% variation from the nominal value unless otherwise indicated or inferred. For example, in certain applications, such as pH measurements, the term "about" can refer to a ±5%, or a ±2.5%, or a ±1% variation from the nominal value or a fixed variation from the nominal value, for example, ±0.1 pH units or ±0.2 pH units.

The present disclosure provides the pharmaceutical compositions that include the furosemide or a therapeutic combination including furosemide, and one or more pharmaceutically acceptable carriers, excipients, or diluents such as a buffer. The excipients may include sodium chloride, sodium hydroxide, water, glycerol, mannitol, sodium phosphate, sodium carbonate, lactose, dextrose and other electrolytes.

Examples of such carriers are well known to skilled artisan and can be prepared in accordance with acceptable pharmaceutical procedures such as, for example, those described in Remington: The Science and Practice of Pharmacy, 20th edition, ed. Alfonso R. Gennaro (Lippincott Williams & Wilkins, Baltimore, Md. (2000)). For example, liquid media or liquid carriers (which are used interchangeably herein) can be used in preparing the pharmaceutical compositions of the present disclosure such as solutions, suspensions, and emulsions. A compound described herein can be dissolved or suspended in a pharmaceutically acceptable liquid carrier such as a buffer, an organic solvent, and/or pharmaceutically acceptable oils and/or fats.

The pharmaceutical compositions of the present disclosure can include other suitable pharmaceutical additives such as solubilizers, emulsifiers, buffers, preservatives, suspending agents, thickening agents, colors, viscosity regulators, stabilizers, adsorbents, binders, antioxidants, bulking agents, pH adjusting agents, preservative, solvent, fluidizing agents and osmo-regulators. As the present disclosure provides the pharmaceutical compositions and their intended use is with the patients, each of the ingredients or compounds of the pharmaceutical compositions described herein can be a pharmaceutically acceptable ingredient or compound.

The use of the singular herein includes the plural (and vice versa) unless specifically stated otherwise.

It is understood that the order of steps or order for performing certain actions can be changed so long as the intended result is obtained. Moreover, two or more steps or actions may be conducted simultaneously.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps Pharmaceutical Compositions Containing Furosemide and Methods of Treatment The present disclosure provides the pharmaceutical composition and methods of treatment with the pharmaceutical composition containing the furosemide and the cyclodextrin or cyclodextrin derivatives for administration to a patient with strikingly higher aqueous solubility at lower pH with enhanced drug stability, reduced drug irritation, and reduced drug incompatibility when used with other infusion formulations.

Cyclodextrins

Cyclodextrins are cyclic carbohydrates that differ from one another by the number of gluco-pyranose units in the structure. The cyclodextrin structure provides a molecule shape like a truncated cone with a hydrophilic exterior surface and hydrophobic interior cavity. These properties make cyclodextrins very valuable for drug administration. The hydrophilic surface provides cyclodextrins with good water solubility and the hydrophobic cavity creates a suitable position to include a drug molecule. A variety of non-covalent forces, such as van der Waals forces, hydrophobic interactions and other forces are responsible for the formation of stable complexes of cyclodextrins and drug molecule. Many processes are used to form cyclodextrin-drug complexes, such as co-precipitation, heating, extrusion, dry mixing, damp mixing, slurry complexation, and paste complexation. Oral uses of the naturally occurring cyclodextrins is well-known with limited parenteral use and applications. Therefore, modified forms of cyclodextrins are generally used in parenteral and other routes of administration for higher stability and bioavailability.

One such modified cyclodextrin is captisol, which is an anionic β-cyclodextrin derivative with sodium sulfate salt separated from the hydrophobic cavity with a butyl ether spacer group. Parenteral studies with captisol demonstrate a substantially higher safety profile with substantially higher complexation characteristics and water stability greater than 35 times over the parent cyclodextrin.

Exemplary cylcodextrins for use in the present pharmaceutical compositions include, for example, a beta-cyclodextrin, a gamma-cyclodextrin, a sulfobutyl-ether-beta-cyclodextrin, a hydroxy-propyl-beta-cyclodextrin, and a randomly methylated beta-cyclodextrin.

Pharmaceutical Compositions Containing Furosemide

The present disclosure relates to the pharmaceutical composition of the furosemide and the cyclodextrin or derivatives thereof, such as β-cyclodextrin derivative (e.g., captisol). The route of administration for the pharmaceutical composition can be parenteral, more specifically, subcutaneous and intravenous route. The specific amount of the cyclodextrin is less than or equal to about 50% of the pharmaceutical composition and the pH values achieved from about 7.0 to about 8.5. As such, one advantage of the disclosure is that furosemide can be administered by subcutaneous infusion or injection to the patient in need thereof. Another advantage of the present disclosure is the ability to administer a therapeutic dose of the furosemide such as 80 mg within the standardized volume of a common cartridge used in drug delivery, i.e., 3-5 mL, to the patient using an infusion device, such as a patch pump. Yet another advantage of the present disclosure is the ability to administer a therapeutic dose of the furosemide, such as 50 mg, by means of an injection device such as an autoinjector. Yet another advantage of the present disclosure is the use in intravenous infusion when other infusion fluids are used concurrently or sequentially without the need for line flushing before and after administration of furosemide. Yet another advantage of the present disclosure is that the pharmaceutical composition remains stable at the pH value from about 7.0 to about 8.3 and is compatible for subcutaneous or intravenous administration of the furosemide with effective delivery and minimal or negligible adverse toxicological effects.

In one embodiment of the present disclosure, the pharmaceutical composition remains stable at the pH value of from about 7.0 to about 8.5. In certain embodiments of the present disclosure, the pharmaceutical composition remains stable at the pH value from 7.2 to 7.6 for subcutaneous or intravenous administration of furosemide.

The furosemide can be present in the pharmaceutical composition as furosemide or in the form of any variations of analogs such as a pharmaceutically acceptable salt, hydrate or an ester. In certain embodiments, the amount of the furosemide in the pharmaceutical composition is from about 8 mg/mL to about 40 mg/mL. In some embodiments, the amount of the furosemide is from about 15 mg/mL to about 26 mg/mL. The pharmaceutical composition further contains the cyclodextrin or derivatives thereof at an amount of less than or equal to 50% and maintain the pH value of the pharmaceutical composition from about 7.0 to about 8.5. In certain embodiments, the pH value of the pharmaceutical composition is maintained from about 7.2 to about 7.6.

In certain embodiments, the amount of the furosemide in the pharmaceutical composition is from about 8 mg/mL to about 40 mg/mL and the cyclodextrin is included in the pharmaceutical composition at an amount less than or equal to 50%. The pH value of the pharmaceutical composition is maintained from about 7.2 to about 7.6. One advantage of the combination of the ingredients in the disclosed amounts and at the disclosed conditions is that therapeutic dose of the furosemide such as 80 mg can be accommodated within a standard size cartridge of the patch pump, e.g., 3-5 mL, and administered to the patient, or self-administered by the patient using, for example, the patch pump.

In some embodiments, the amount of the furosemide in the pharmaceutical composition is from about 8 mg/mL to about 40 mg/mL. In certain embodiments, the amount of the sulfobutyl ether derivative of β-cyclodextrin (e.g., captisol), in the pharmaceutical composition is less than or equal to 50%. In certain embodiments, the pH value of the pharmaceutical composition is from about 7.0 to about 8.5. In yet another embodiment, the above pharmaceutical composition is administered to the patient subcutaneously or intravenously as needed.

In another embodiment, the present disclosure provides a pharmaceutical composition, comprising:

from about 40 mM to about 160 mM of a diuretic selected from the group consisting of 4-chloro-2-((furan-2-ylmethyl) amino)-5-sulfamoylbenzoic acid, a pharmaceutically acceptable salt thereof, and a mixture of the foregoing;

from about 45 mM to about 190 mM of a sulfobutyl ether derivative of β-cyclodextrin; and water; wherein the pharmaceutical composition has a pH value from about 7.0 to about 8.5.

The pharmaceutical composition can be further characterized according to the amount of sulfobutyl ether derivative of β-cyclodextrin. For example, in certain embodiments, the pharmaceutical composition comprises from about 120 mM to about 160 mM of a sulfobutyl ether derivative of β-cyclodextrin. In certain embodiments, the pharmaceutical composition comprises from about 135 mM to about 145 mM of a sulfobutyl ether derivative of β-cyclodextrin. In certain embodiments, the sulfobutyl ether derivative of β-cyclodextrin is sulfobutyl ether beta-cyclodextrin sodium.

The pharmaceutical composition can be further characterized according to the amount of diuretic. For example, in certain embodiments, the pharmaceutical composition comprises from about 80 mM to about 100 mM of the diuretic. In certain embodiments, the pharmaceutical composition comprises about 91 mM of the diuretic.

In certain embodiments, the pharmaceutical composition further comprises a buffer. In certain embodiments, the buffer comprises tris(hydroxymethyl)aminomethane. In certain embodiments, the buffer is present in an amount ranging from about 1 mM to about 50 mM. In certain embodiments, the buffer is present in an amount of about 25 mM.

In certain embodiments, the pharmaceutical composition has a pH of from about 7.0 to about 8.0. In certain embodiments, the pharmaceutical composition has a pH of about 7.4.

In certain embodiments, the pharmaceutical composition contains at least 50% (w/w) water.

The pharmaceutical composition of the present disclosure contains the furosemide with high solubility and enhanced stability, which advantageously enables administration of a higher dose of the furosemide in lower volume of the pharmaceutical composition. The pharmaceutical composition of the present disclosure achieves the administration of the higher concentration of the furosemide at a pH value that is compatible for subcutaneous administration to the patient. More specifically, the pharmaceutical composition is stable and suitable for subcutaneous or intravenous administration.

In some embodiments, the present disclosure includes the pharmaceutical composition of the furosemide at a higher concentration in a drug volume of 2-20 mL. In another embodiment, the amount of the cyclodextrin in the pharmaceutical composition is less than or equal to 50%. In yet another embodiment, the pharmaceutical composition has the pH value from about 7.0 to about 8.5 compatible for subcutaneous and intravenous administration.

In some embodiments, the present disclosure includes the pharmaceutical composition of the furosemide and the cyclodextrin or cyclodextrin derivative, such as captisol, at an amount from about 40% to about 50%.

Methods of Treatment

In another embodiment, the present disclosure includes a method of treating the patient with or exhibiting symptoms of edema, heart failure, kidney or liver disease by administering to the patient the pharmaceutical composition containing furosemide, or the pharmaceutically acceptable salt, hydrate or ester thereof. More particularly, the pharmaceutical composition contains furosemide, or the pharmaceutically acceptable salt, hydrate or ester thereof at an amount of about 30 mg/mL. The pharmaceutical composition further contains the cyclodextrin at an amount of less than or equal to 50% in the pharmaceutical composition.

In one embodiment, the pharmaceutical composition is administered to the patient subcutaneously. Specifically, the pharmaceutical composition is administered to the patient subcutaneously using a pump device or an injection device. The pump device can include, for example, a patch device. The injection device can include, for example, an auto injector device. In another embodiment, the pharmaceutical composition is administered to the patient intravenously. Specifically, the pharmaceutical composition is administered to the patient intravenously using the pump device or the injection device. In various embodiments, the pharmaceutical composition is administered to the patient subcutaneously or intravenously using the patch device or the auto injector device. In some embodiments, the present disclosure includes the method of treating the patient with or exhibiting symptoms of edema, heart failure, kidney or liver disease by administering to the patient the pharmaceutical composition of furosemide, or the pharmaceutically acceptable salt, hydrate or furosemide ester with an amount of the furosemide in the pharmaceutical composition to about 40 mg/mL. The pharmaceutical composition further contains the cyclodextrin or derivatives thereof at an amount of less than or equal to 50% at the pH value of the pharmaceutical composition from about 7.2 and about 7.6. In one embodiment, the cyclodextrin is a β-cyclodextrin. In another embodiment the cyclodextrin is a sulfobutyl ether derivative of β-cyclodextrin. In yet another embodiment, the sulfobutyl ether derivative of β-cyclodextrin is captisol. In one embodiment, the pH value of the pharmaceutical composition is from about 7.0 to about 7.8. In certain embodiments, the pH value is maintained from about 7.0 to about 8.3.

In an embodiment, the patient suffering from edema, heart failure, kidney or liver disease or exhibiting such symptoms thereof is administered with the pharmaceutical composition with the amount of the furosemide from about 8 mg/mL to about 40 mg/mL. In another embodiment, the amount of the captisol in the pharmaceutical composition is less than or equal to 50%. In another embodiment, the pH of the pharmaceutical composition is from about 7.0 to about 8.5.

In another embodiment, the present disclosure provides a method of treating a patient suffering from a condition selected from edema, heart failure, kidney disease, or liver disease, or having a symptom any of the foregoing, comprising administering to the patient in need thereof a therapeutically effective amount of a pharmaceutical composition of described herein treat the condition. In certain embodiments, the condition is edema. In certain embodiments, the condition is heart failure. In certain embodiments, the condition is kidney disease or liver disease.

In some embodiments, the pharmaceutical composition is administered to the patient parenterally including subcutaneous or intravenous administration. In the present disclosure, several devices can be used to facilitate self-administration of the pharmaceutical composition. The device typically includes a reservoir or a cartridge, for example, pre-loaded with the pharmaceutical composition to be administered, or inserted into the device prior to its use. For example, a micropump can provide precise parenteral administration of desired quantities of a liquid pharmaceutical composition. Another type of device useful for parenteral delivery or administration of pharmaceutical composition is often referred to as the pump device or the injection device.

In some embodiments, the present disclosure includes medical devices of a unitary construction. Such medical devices can be for a single use. In certain embodiments, the medical device can be of a multi-piece construction. In such medical devices, a disposable or a reusable portion or component can be present. For example, a housing defining or including the reservoir can be a disposable or a reusable component of the medical device.

The patch pump or patch device of the present disclosure may include a pump device having a drug reservoir and electrolytically, manually, mechanically, automatically or electronically driven piston. The drug pump device may be furnished with a prefilled cartridge. If a glass cartridge or cartridge of other suitable pharmaceutical-grade composite material is used, the drugs can be stored in the pump device for long-term shelf life or inserted into the device just prior to use. The drug pump device may be implantable, include an adhesive patch for adhesion to patient's skin, or may be worn on a belt or is attached to the body by a strap or by other means.

Additional Features of Pharmaceutical Compositions and Methods of Treatment

The pharmaceutical forms of the present disclosure suitable for injection can include sterile aqueous solutions or dispersions for the extemporaneous preparation of sterile injectable solutions or dispersions. In certain embodiments, the pharmaceutical form is sterile, and its viscosity permits it to flow through an infusion line or needle. The pharmaceutical form should be stable under the conditions of manufacture and storage, for example, preserved against the contaminating action of microorganisms, if needed. The carrier can be a solvent or dispersion medium containing liquids such as water, ethanol, polyol (for example, glycerol, propylene glycol, and liquid polyethylene glycol), suitable mixtures thereof, and vegetable oils.

In the present disclosure, the pharmaceutical compositions can achieve higher level of the furosemide suitable for administration. For example, the amount of the furosemide in the pharmaceutical composition can be about 8 mg/mL or greater, about 10 mg/mL or greater, or about 15 mg/mL or greater. In various embodiments, the amount of the furosemide can be about 15 mg/mL or greater, about 20 mg/mL or greater, about 26 mg/mL or greater, or about 30 mg/mL, or about 40 mg/mL.

Concentration of Furosemide

In some embodiments, the furosemide can be present in an amount from about 8 mg/mL to about 40 mg/mL, about 10 mg/mL to about 26 mg/mL, from about 10 mg/mL to about 30 mg/mL, from about 10 mg/mL to about 15 mg/mL, from about 15 mg/mL to about 40 mg/mL, from about 16 mg/mL to about 24 mg/mL, from about 20 mg/mL to about 40 mg/mL.

Disorders for Treatment

In the present disclosure, furosemide, therapeutic combinations, and pharmaceutical compositions can be useful for treating a pathological condition or disorder or symptoms in the patient. The present disclosure provides administering higher concentrations of the furosemide parenterally to alleviate the disorders, such as edema, heart failure, kidney or liver disease or having such symptoms. The present disclosure accordingly includes the method of providing to the patient the pharmaceutical composition that includes a compound or therapeutic combination of the present disclosure in combination or association with a pharmaceutically acceptable carrier or solubilizer or a suitable buffer. Compounds and therapeutic combinations of the present disclosure can be administered alone or in combination with other therapeutically effective compounds or therapies for the treatment of a pathological condition or disorder.

The present disclosure also includes the methods of administration of the pharmaceutical composition including the furosemide or one or more of its analogues or variations or precursors to the patient with edema related disease or disorder. The edema related disease or disorder may also include heart failure, chronic kidney disease.

pH of Pharmaceutical Composition

In certain embodiments, the pharmaceutical composition can have the pH value in the range of about 7.0 to about 8.7. In certain embodiments, the pharmaceutical formulations can have the pH value in the range of about 7.0 to about 8.5, or about 7.2 to about 7.6 or about 7.3 to about 7.8. In some embodiments, the pharmaceutical composition can have the pH value in the range of about 7.4 to about 8.0, or about 7.4 to about 9.0.

Amount of Cyclodextrin

Further, in various embodiments, the cyclodextrin in the pharmaceutical composition can be less than or equal to about 50%. In some embodiments, the cyclodextrin in the pharmaceutical composition can be less than or equal to about 50%. In some embodiments, the amount of the cyclodextrin can be less than or equal to about 35%, less than or equal to about 30%, or less than or equal to about 25%. In certain embodiments, the amount of the cyclodextrin can be in a range of about 5% to about 50%, about 40% to about 50%, about 20% to about 40%, or about 20% to about 30%. In certain embodiments, the amount of the cyclodextrin can be about 10% or about 40%.

Further, in certain embodiments, the cyclodextrin in the pharmaceutical composition can be less than or equal to about 45% (w/w). In some embodiments, the cyclodextrin in the pharmaceutical composition can be less than or equal to about 40% (w/w). In some embodiments, the amount of the cyclodextrin can be less than or equal to about 35%, less than or equal to about 20% (w/w), or less than or equal to about 15% (w/w). In certain embodiments, the amount of the cyclodextrin can be in a range of about 10% (w/w) to about 50% (w/w), about 35% (w/w) to about 50% (w/w), about 25% (w/w) to about 40% (w/w), or about 25% (w/w) to about 30% (w/w). In certain embodiments, the amount of the cyclodextrin can be in a range of about 20% (w/w) to about 30% (w/w). In certain embodiments, the amount of the cyclodextrin can be about 15% (w/w) or about 45% (w/w).

The amount of cyclodextrin in the pharmaceutical composition may be characterized according to the molar ratio of cyclodextrin to furosemide in the pharmaceutical composition. For example, in certain embodiments, the molar ratio of cyclodextrin (e.g., captisol) to furosemide is greater than about 1, 2, 3, 4, 5, 6, 7, 8, 9, 10, 11, 12, 13, 14, or 15. In certain embodiments, the molar ratio of cyclodextrin to furosemide is greater than about 2. In certain embodiments, the molar ratio of cyclodextrin to furosemide is greater than about 3. In certain other embodiments, the molar ratio of cyclodextrin to furosemide is from 2:1 to about 15:1. In certain other embodiments, the molar ratio of cyclodextrin to furosemide is from 2:1 to about 3:1. In certain other embodiments, the molar ratio of cyclodextrin to furosemide is from 2:1 to about 5:1. In certain other embodiments, the molar ratio of cyclodextrin to furosemide is from 5:1 to about 10:1

Therapeutic Benefits

In the present disclosure, the pharmaceutical composition may reduce the disease condition and symptoms by at least about 5% to at least about 99% as compared to an untreated patient. The compound may be administered to the patients in various forms including, an injection, a transdermal patch, and sustained-release formulations. The composition may be administered via enteral or parenteral route including, intravenous, subcutaneous, topical, transdermal, intradermal, transmucosal, intraperitoneal, intramuscular, intracapsular, intraorbital, intracardiac, transtracheal, subcuticular, intraarticular, subcapsular, subarachnoid, intraspinal, epidural and intrasternal injection and infusion.

The typical dosages of the compounds and the compositions of the present disclosure may vary within a wide range depending on many factors, including but not limited to, route of administration, treatment stage, pretreatment use of oral medications, body weight, age and general condition of the patient.

Amount of Water in the Pharmaceutical Composition

The pharmaceutical composition may be further characterized according to the amount of water in the pharmaceutical composition. In certain embodiments, pharmaceutical composition comprises at least 40% (w/w), 45% (w/w), 50% (w/w), 55% (w/w), 60% (w/w), 65% (w/w), 70% (w/w), 75% (w/w), 80% (w/w), or 85% (w/w) water. In certain embodiments, pharmaceutical composition comprises at least 90% (w/w), 91% (w/w), 92% (w/w), 93% (w/w), 94% (w/w), 95% (w/w), 96% (w/w), 97% (w/w), 98% (w/w), or 99% (w/w) water. In certain embodiments, pharmaceutical composition comprises at least 50% (w/w). In certain embodiments, pharmaceutical composition comprises at least 55% (w/w). In certain embodiments, pharmaceutical composition comprises at least 60% (w/w). In certain embodiments, pharmaceutical composition comprises at least 65% (w/w). In certain embodiments, pharmaceutical composition comprises at least 95% (w/w) water. In certain embodiments, pharmaceutical composition comprises at least 96% (w/w) water. In certain embodiments, pharmaceutical composition comprises at least 97% (w/w) water. In certain embodiments, pharmaceutical composition comprises at least 98% (w/w) water. In certain embodiments, pharmaceutical composition comprises at least 99% (w/w) water. In certain embodiments, the pharmaceutical composition comprises from about 50% (w/w) to about 70% (w/w) water. In certain embodiments, the pharmaceutical composition comprises from about 60% (w/w) to about 70% (w/w) water.

Buffer

In certain embodiments, the pharmaceutical composition comprises a buffer. In certain embodiments, buffer is present in the pharmaceutical composition in an amount less than about 1% (w/w), 2% (w/w), 3% (w/w), 4% (w/w), 5% (w/w), 6% (w/w), 7% (w/w), 8% (w/w), 9% (w/w), or 10% (w/w). In certain embodiments, the buffer may comprise phosphoric acid, citric acid, acetic acid, histidine, lactic acid, tromethamine, gluconic acid, aspartic acid, glutamic acid, tartaric acid, succinic acid, malic acid, fumaric acid, or alpha-ketoglutaric acid.

Additional Components of the Pharmaceutical Composition

The pharmaceutical composition of the present disclosure may also contain adjuvants, diluents, excipients and/or carriers, known in the art, compatible with the compounds and the other ingredients of the pharmaceutical composition, and not deleterious to the recipient thereof.

Stability of the Pharmaceutical Compositions

The pharmaceutical composition may be further characterized according to stability of the pharmaceutical composition to storage. This can be achieved by storing a pharmaceutical composition at a designated temperature for a duration of time, then removing an aliquot of the pharmaceutical composition, and analyzing the aliquot to determine if any components in the original pharmaceutical composition have degraded. For example, the aliquot can be subjected to visual analysis to determine the presence of any undissolved solids and/or a change in color or clarity of the solution. Also, the aliquot can be analyzed to determine the amount of diuretic present (e.g., furosemide or a pharmaceutically acceptable salt thereof) relative to the original amount of diuretic in the pharmaceutical composition.

Accordingly, in certain embodiments, less than 4% of the diuretic degrades upon storage of the pharmaceutical composition at 40° C. for 29 days. In certain embodiments, less than 1% of the diuretic degrades upon storage of the pharmaceutical composition at 40° C. for 29 days. In certain embodiments, less than 0.5% of the diuretic degrades upon storage of the pharmaceutical composition at 40° C. for 29 days. In certain embodiments, less than 0.1% of the diuretic degrades upon storage of the pharmaceutical composition at 40° C. for 29 days. In certain embodiments, less than 10% of the diuretic degrades upon storage of the pharmaceutical composition at 70° C. for 29 days. In certain embodiments, less than 7% of the diuretic degrades upon storage of the pharmaceutical composition at 70° C. for 29 days. In certain embodiments, less than 5% of the diuretic degrades upon storage of the pharmaceutical composition at 70° C. for 29 days. In certain embodiments, less than 3% of the diuretic degrades upon storage of the pharmaceutical composition at 70° C. for 29 days. In certain embodiments, less than 1% of the diuretic degrades upon storage of the pharmaceutical composition at 70° C. for 29 days. In certain embodiments, less than 3% of the diuretic degrades upon storage of the pharmaceutical composition at 25° C. for 24 months. In certain embodiments, less than 2% of the diuretic degrades upon storage of the pharmaceutical composition at 25° C. for 24 months. In certain embodiments, less than 1% of the diuretic degrades upon storage of the pharmaceutical composition at 25° C. for 24 months. In certain embodiments, less than 0.5% of the diuretic degrades upon storage of the pharmaceutical composition at 25° C. for 24 months. In certain embodiments, less than 0.1% of the diuretic degrades upon storage of the pharmaceutical composition at 25° C. for 24 months. In certain embodiments, less than 0.05% of the diuretic degrades upon storage of the pharmaceutical composition at 25° C. for 24 months.

Additionally, in certain embodiments, the pharmaceutical composition is characterized by the purity of the diuretic in the pharmaceutical composition upon storage. For example, in certain embodiments, the after storage of the pharmaceutical composition at 40° C. for 29 days the diuretic has a purity of at least 97%. In certain embodiments, after storage of the pharmaceutical composition at 40° C. for 29 days the diuretic has a purity of at least 98%. In certain embodiments, after storage of the pharmaceutical composition at 40° C. for 29 days the diuretic has a purity of at least 99%. In certain embodiments, after storage of the pharmaceutical composition at 40° C. for 29 days the diuretic has a purity of at least 99.5%. In certain embodiments, after storage of the pharmaceutical composition at 40° C. for 29 days the diuretic has a purity of at least 99.9%. In certain embodiments, the after storage of the pharmaceutical composition at 70° C. for 29 days the diuretic has a purity of at least 95%. In certain embodiments, after storage of the pharmaceutical composition at 70° C. for 29 days the diuretic has a purity of at least 97%. In certain embodiments, after storage of the pharmaceutical composition at 70° C. for 29 days the diuretic has a purity of at least 98%. In certain embodiments, after storage of the pharmaceutical composition at 70° C. for 29 days the diuretic has a purity of at least 99%. In certain embodiments, after storage of the pharmaceutical composition at 70° C. for 29 days the diuretic has a purity of at least 99.5%. In certain embodiments, the after storage of the pharmaceutical composition at 25° C. for 24 months the diuretic has a purity of at least 97%. In certain embodiments, after storage of the pharmaceutical composition at 25° C. for 24 months the diuretic has a purity of at least 98%. In certain embodiments, after storage of the pharmaceutical composition at 25° C. for 24 months the diuretic has a purity of at least 99%. In certain embodiments, after storage of the pharmaceutical composition at 25° C. for 24 months the diuretic has a purity of at least 99.5%. In certain embodiments, after storage of the pharmaceutical composition at 25° C. for 24 months the diuretic has a purity of at least 99.9%.

Exemplary Benefits of the Pharmaceutical Compositions

Various embodiments of the present disclosure enable administration of higher concentrations of the furosemide to the patient. Further, the pharmaceutical composition of various embodiments of the present disclosure has the pH appropriate for subcutaneous or intravenous administration of the composition to the patient.

Another advantage of the embodiments of the present disclosure is that the pharmaceutical compositions with higher concentration of the furosemide and lower amount of the captisol can be administered with the pump device or the injection device.

Yet another advantage of the pharmaceutical compositions of the present disclosure is substantially high solubility at a desired pH, which may facilitate intravenous infusion by allowing co-administration with other infusion fluids or pharmaceutical formulations.

It has been observed that the furosemide demonstrates higher solubility and enhanced stability in pharmaceutical compositions in combination with the cyclodextrins or cyclodextrin derivatives such as sulfobutyl ether derivative of β-cyclodextrin compared to other excipients with the furosemide for treatment of edema, hypertension and other renal diseases.

Unit Container

Another aspect of the disclosure provides a unit container comprising a pharmaceutical composition described herein. In certain embodiments, the container contains from about 1 mL to about 10 mL, from about 1 mL to about 5 mL, from about 1 mL to about 4 mL, from about 1 mL to about 3 mL, from about 1 mL to about 2 mL, from about 1 mL to about 1.5 mL, from about 2 mL to about 5 mL, or from about 2 mL to about 3 mL of pharmaceutical composition. In certain embodiments, the container contains from about 1 mL to about 3 mL of pharmaceutical composition. In certain embodiments, the container contains from about 2 mL to about 3 mL of pharmaceutical composition. In certain embodiments, the container contains from about 5 mL to about 10 mL of pharmaceutical composition. In certain embodiments, the container contains from about 8 mL to about 10 mL of pharmaceutical composition.

Medical Kits

Another aspect of the invention provides a medical kit comprising, for example, (i) a pharmaceutical composition described herein, and (ii) instructions for use, such as for use in a method described herein.

It is understood that the examples, embodiments and teachings presented in this application are described merely for illustrative purposes. Any variations or modifications thereof are to be included within the scope of the present application as discussed.

EXAMPLES

The invention now being generally described, will be more readily understood by reference to the following examples, which are included merely for purposes of illustration of certain aspects and embodiments of the present invention, and are not intended to limit the invention.

Example 1—Preparation of Exemplary Aqueous Furosemide Formulation

An exemplary aqueous furosemide formulation was prepared according to the procedure set forth below. The aqueous furosemide formulation contained furosemide at a concentration of 30 mg/mL, captisol at a concentration of about 300 mg/mL, and tris(hydroxymethyl)aminomethane buffer at a concentration of 25 mM. The formulation had a pH of 7.4.

Captisol (157.65 g, 5.1% water, USP grade, Hovione) was slowly added over about 6.5 minutes (to facilitate dissolution and avoid clumping), while stirring with a magnetic stir bar, to approximately 350 mL of water for injection (Rocky Mountain Biologics, Product No. WIFI-USP-1X6) in a 1-L beaker. Tris(hydroxymethyl) aminomethane free-base (1.514 g, Sigma, Product No. 101974108) was added over about 3 minutes, then 3.6 mL of 10 N NaOH solution (Fisher, Product No. S71993-1) was added over about 2.5 minutes. Furosemide (15.0 g, USP grade, Spectrum, Product No. F1133) was added slowly and dissolved over about one hour, with addition of about 5 µL 10 N NaOH (to maintain pH in the range of 7.4-7.5), and sonication (at 26-28 minutes, 31-36 minutes, 38-43 minutes, and 50-55 minutes during the one hour dissolution period). The solution was poured from the beaker into a 500-mL volumetric flask. The beaker was rinsed with approximately 20 mL of water for injection, which was then added to the volumetric flask. The solution was diluted to nearly 500 mL with water for injection, and the pH was determined to that it was in the range of 7.4-7.5. The solution was diluted to 500 mL with water for injection, and the pH was determined to be 7.408. Finally, the solution was filtered through an Argos Bottle-Top Filter System (Product No. BPV2250) in a laminar flow hood.

Example 2—Stability Analysis of Exemplary Furosemide Formulation

A stability analysis was conducted on exemplary furosemide formulations prepared using procedures similar to that described in Example 1. Experimental procedures and results are provided below.

Part I—Experimental Procedures

Aqueous furosemide formulations A-H described in Table 1, below, were prepared according to the following general procedure. The required amounts of captisol (50, 100, or 150 grams) and tris(hydroxymethyl)aminomethane free-base (1.5 g, in formulations where it was included) were added to a 500-mL volumetric flask. Water for injection (about 350 mL) was added, and the solids were dissolved by shaking and/or swirling the flask. Sodium hydroxide (10 N) was added in an amount sufficient to deprotonate the carboxylic acid group of furosemide (3.6 mL for formulations with, and 4.5 mL for formulations without, tris(hydroxymethyl) aminomethane free-base). Furosemide (15 g) was added, and the mixture was mixed by swirling, shaking, and/or sonication for about 10 minutes. Sodium hydroxide (1 N or 10 N) was added dropwise to adjust the pH to the desired value (7.4 or 8.4). The solution was diluted to 500 mL with water for injection, then filtered into vials or bottles through a Millex-GV 33 mm hydrophilic PVDF membrane syringe filter (0.22 µm pore size). More than one filter was used to filter the entire 500-mL solution, and the first few drops through each filter were discarded.

Aliquots of the furosemide formulation (10 mL) were added to 12-mL glass vials (Fisherbrand Type 1 Class A Clear Borosilicate Glass Sample Vials), and the vials were sealed with black phenolic caps with PTFE-faced white rubber liner. Then, the vials were stored in an oven at 25° C., 40° C., and 60° C. for a specified duration of time (e.g., 1 week). After storage for either 1 week, 2 weeks, 1 month, 2 months, 3 months, or 6 months a vial was removed from the oven and the furosemide formulation was analyzed for visual appearance, pH, and to determine the amount of furosemide and/or impurities in the formulation. Analysis of impurities included determination of the amount of impurities 2-chloro-4-furfurylamino-5-sulfamoylbenzoic acid and 4-chloro-5-sulfamoylanthranilic acid, respectively designated as Peak A and Peak B in the Tables below and HPLC chromatograms in FIG. 1.

Analysis by HPLC was conducted according to the methods described in Table 2, below, following dilutions of the formulations. Samples for HPLC analysis were diluted by a factor of 1,000 (serial dilutions by a factor of 100 and 10, to a concentration of ~30 µg/mL furosemide) or a factor of 60 (to a concentration of ~500 µg/mL furosemide), as specified in the description and tables below. The diluent was 1:1 methanol:pH 5.7 buffer (prepared with 1,000 mL MQ water, 750 µL triethylamine, 250 µL formic acid, and adjusted to pH 5.7 with triethylamine).

Part II—Results

Results of the stability analysis are provided in Tables 3-24 below. Representative HPLC chromatograms for analyzed samples of selected furosemide formulations are depicted in FIG. 1 (analyte detection analysis was performed at 270 nm). All values determined by HPLC (i.e., in Tables 3-6, 11-13, and 18-20) are the average of results from three HPLC chromatograms obtained from a given sample.

Data in Tables 3, 11, and 18 for furosemide concentration as a percentage of theoretical (i.e., 30 mg/mL) were calculated based on a standard calibration curve and were obtained from HPLC samples that had been diluted by a factor of 1,000. Data in Tables 4-6, 12, 13, 19, and 20 for the area percentage of the furosemide peak, Peak A, or Peak B (versus the total area of all peaks integrated in the chromatogram) were obtained from HPLC samples that had been diluted by either a factor of 1,000 (for storage duration of 0 days, 1 week, 2 weeks, and 1 month) or a factor of 60 (for storage duration of 2, 3, or 6 months).

TABLE 1

Aqueous Furosemide Formulations Subjected to Stability Studies

| Formulation | Furosemide (mg/mL) | Captisol (mg/mL) | Tris Buffer (mg/mL) | pH |
| --- | --- | --- | --- | --- |
| A | 30 | 100 | 25 | 7.4 |
| B | 30 | 200 | 25 | 7.4 |
| C | 30 | 300 | 25 | 7.4 |
| D | 30 | 200 | 25 | 8.4 |
| E | 30 | 100 | 0 | 7.4 |
| F | 30 | 200 | 0 | 7.4 |
| G | 30 | 300 | 0 | 7.4 |
| H | 30 | 200* | 0 | 7.4 |

*Formulation H was prepared with Captisol buffered with sodium phosphate.

TABLE 2

HPLC Methods for Analytical Analysis of Stored Furosemide Formulations

HPLC Method for Storage Durations of 0 days, 1 week, 2 weeks, 1 month, and 2 months

| | | |
| --- | --- | --- |
| Column information | Name | Zorbax-RX C18, 5 µm, 4.6 mm × 150 mm |
| | Catalog # | 883967-902 |
| Mobile Phase A | | pH 5.7 buffer (1,000 mL MQ water, 750 µL triethylamine, 250 µL formic acid, adjusted to pH 5.7 with triethylamine) |

TABLE 2-continued

HPLC Methods for Analytical Analysis of Stored Furosemide Formulations

| | |
|---|---|
| Mobile Phase B | Acetonitrile |
| Flow rate | 0.8 mL/min |
| Column temperature | Ambient |
| Autosampler temperature | Ambient |
| Injection volume | 5.0 μL |
| Detector wavelength | 270 nm |

| Gradient | Time (minutes) | % Mobile Phase B |
|---|---|---|
| | 0.0 | 8 |
| | 1.0 | 8 |
| | 3.0 | 25 |
| | 10.5 | 40 |
| | 11.5 | 40 |
| | 12.0 | 8 |
| | 15.0 | End |

HPLC Method for Storage Duration of 3 months

| | | |
|---|---|---|
| Column information | Name | Zorbax-RX C18, 5 μm, 4.6 mm × 150 mm |
| | Catalog # | 883967-902 |
| Mobile Phase A | | pH 5.7 buffer (1,000 mL MQ water, 750 μL triethylamine, 250 μL formic acid, adjusted to pH 5.7 with triethylamine) |
| Mobile Phase B | | Acetonitrile |
| Flow rate | | 1.0 mL/min |
| Column temperature | | Ambient |
| Autosampler temperature | | Ambient |
| Injection volume | | 5.0 μL |
| Detector wavelength | | 270 nm |

| Gradient | Time (minutes) | % Mobile Phase B |
|---|---|---|
| | 0.0 | 5 |
| | 2.0 | 5 |
| | 4.0 | 25 |
| | 10.5 | 40 |
| | 11.5 | 40 |
| | 12.0 | 5 |
| | 16.5 | End |

HPLC Method for Storage Duration of 6 months

| | | |
|---|---|---|
| Column | Name | Zorbax-RX C18, 5 μm, 4.6 mm × 150 mm |
| | Catalog # | 883967-902 |
| Mobile Phase A | | 10 mM KH$_2$PO$_4$ in Water (pH 4.77, unadjusted) |
| Mobile Phase B | | Acetonitrile |
| Flow rate | | 1.0 mL/min |
| Column temperature | | Ambient |
| Autosampler temperature | | Ambient |
| Injection volume | | 5.0 μL |
| Detector wavelength | | 270 nm |

| Gradient | Time (minutes) | % Mobile Phase B |
|---|---|---|
| | 0.0 | 5 |
| | 2.0 | 5 |
| | 3.0 | 25 |
| | 15 | 30 |
| | 15.5 | 50 |
| | 16.0 | 50 |
| | 16.5 | 5 |
| | 20 | End |

TABLE 3

Furosemide Concentration as a Percentage of Theoretical (30 mg/mL) for Formulations Stored at 60° C.

| Formu- | Duration of Storage | | | | | |
|---|---|---|---|---|---|---|
| lation | 0 days | 1 week | 2 weeks | 1 month | 2 months | 3 months |
| A | 101.28 | 98.02 | 99.89 | 97.82 | 97.13 | 95.37 |
| B | 100.44 | 100.01 | 100.64 | 98.68 | 100.19 | 98.36 |
| C | 100.45 | 98.90 | 101.74 | 101.14 | 99.67 | 97.07 |
| D | 101.55 | 99.74 | 98.92 | 104.38 | 99.94 | 100.78 |
| E | 100.78 | 101.44 | 100.55 | 99.80 | 99.78 | 95.64 |
| F | 100.32 | 100.13 | 99.92 | 99.04 | 100.22 | 99.10 |
| G | 103.43 | 102.63 | 101.12 | 101.45 | 101.92 | 102.06 |
| H | 101.15 | 101.06 | 99.48 | 100.72 | 100.74 | 98.48 |

TABLE 4

Furosemide Area Percentage of Total Chromatogram for Formulations Stored at 60° C.

| Formu- | Duration of Storage* | | | | | |
|---|---|---|---|---|---|---|
| lation | 0 days | 1 week | 2 weeks | 1 month | 2 months | 3 months |
| A | 100 | 99.223** | 100 | 99.37 | 98.12 | 95.17 |
| B | 100 | 100 | 100 | 100 | 98.78 | 97.01 |
| C | 100 | 100 | 100 | 100 | 99.55 | 98.12 |
| D | 100 | 100 | 100 | 100 | 99.48 | 98.32 |
| E | 100 | 100 | 100 | 100 | 98.84 | 96.08 |
| F | 100 | 100 | 100 | 100 | 99.15 | 97.22 |
| G | 100 | 100 | 100 | 100 | 99.23 | 97.72 |
| H | 100 | 100 | 100 | 100 | 99.08 | 97.44 |

*Samples for HPLC analysis were diluted by a factor of 1,000 (for storage duration of 0 days, 1 week, 2 weeks, and 1 month) or a factor of 60 (for storage duration of 2 months and 3 months).
**Only one of three samples analyzed contained peaks other than furosemide.

TABLE 5

Peak B Area Percentage of Total Chromatogram for Formulations Stored at 60° C.

| Formu- | Duration of Storage* | | | | | |
|---|---|---|---|---|---|---|
| lation | 0 days | 1 week | 2 weeks | 1 month | 2 months | 3 months |
| A | 0 | 0 | 0 | 0.63 | 1.12 | 3.051 |
| B | 0 | 0 | 0 | 0 | 0.68 | 1.913 |
| C | 0 | 0 | 0 | 0 | 0.27 | 1.237 |
| D | 0 | 0 | 0 | 0 | 0.33 | 1.138 |
| E | 0 | 0 | 0 | 0 | 0.72 | 2.473 |
| F | 0 | 0 | 0 | 0 | 0.52 | 1.735 |
| G | 0 | 0 | 0 | 0 | 0.45 | 1.423 |
| H | 0 | 0 | 0 | 0 | 0.59 | 1.615 |

*Samples for HPLC analysis were diluted by a factor of 1,000 (for storage duration of 0 days, 1 week, 2 weeks, and 1 month) or a factor of 60 (for storage duration of 2 months and 3 months).

TABLE 6

Peak A Area Percentage of Total Chromatogram for Formulations Stored at 60° C.

| Formu- | Duration of Storage* | | | | | |
|---|---|---|---|---|---|---|
| lation | 0 days | 1 week | 2 weeks | 1 month | 2 months | 3 months |
| A | 0 | 1.09** | 0 | 0 | 0.10 | 0.082 |
| B | 0 | 0 | 0 | 0 | 0 | 0.028 |
| C | 0 | 0 | 0 | 0 | 0 | 0.011 |
| D | 0 | 0 | 0 | 0 | 0 | 0.013 |
| E | 0 | 0 | 0 | 0 | 0 | 0.034 |
| F | 0 | 0 | 0 | 0 | 0 | 0.027 |

TABLE 6-continued

Peak A Area Percentage of Total Chromatogram for Formulations Stored at 60° C.

| Formu-lation | Duration of Storage* | | | | | |
|---|---|---|---|---|---|---|
| | 0 days | 1 week | 2 weeks | 1 month | 2 months | 3 months |
| G | 0 | 0 | 0 | 0 | 0 | 0.019 |
| H | 0 | 0 | 0 | 0 | 0 | 0.027 |

*Samples for HPLC analysis were diluted by a factor of 1,000 (for storage duration of 0 days, 1 week, 2 weeks, and 1 month) or a factor of 60 (for storage duration of 2 months and 3 months).
**Only one of three samples analyzed contained this peak.

TABLE 7 pH for Formulations Stored at 60° C.

| Formu-lation | Duration of Storage | | | | | |
|---|---|---|---|---|---|---|
| | 0 days | 1 week | 2 weeks | 1 month* | 2 months | 3 months |
| A | 7.492 | 7.456 | 7.454 | 7.02 | 6.893 | 6.798 |
| B | 7.545 | 7.541 | 7.634 | 7.37 | 7.106 | 6.890 |
| C | 7.536 | 7.533 | 7.531 | 7.46 | 7.335 | 7.112 |
| D | 8.426 | 8.414 | 8.427 | 8.31 | 8.387 | 8.213 |
| E | 7.721 | 7.942 | 7.821 | 6.91 | 6.670 | 6.412 |
| F | 7.258 | 7.417 | 7.513 | 7.02 | 6.736 | 6.471 |
| G | 7.499 | 7.380 | 7.361 | 6.93 | 6.623 | 6.394 |
| H | 7.568 | 7.450 | 7.407 | 7.13 | 6.762 | 6.539 |

*A different pH meter was used to measure the samples stored for a duration of 1 month.

TABLE 8

Osmotic Pressure (in mOsm/kg) for Formulations Stored at 60° C.

| Formu-lation | Captisol (mg/mL) | Duration of Storage | | | | | |
|---|---|---|---|---|---|---|---|
| | | 0 days | 1 week | 2 weeks | 1 month | 2 months | 3 months |
| A | 100 | 343 | 342 | 340 | 345 | 346 | 346 |
| B | 200 | 733 | 718 | 759 | 717 | 720 | 734 |
| C | 300 | 1208 | 1285 | 1295 | 1307 | 1369 | 1435 |
| D | 200 | 724 | 762 | 749 | 744 | 736 | 737 |
| E | 100 | 340 | 337 | 339 | 341 | 343 | 342 |
| F | 200 | 721 | 711 | 703 | 722 | 729 | 725 |
| G | 300 | 1274 | 1226 | 1214 | 1192 | 1212 | 1232 |
| H | 200* | 739 | 713 | 723 | 735 | 725 | 724 |

*Formulation H was prepared with Captisol buffered with sodium phosphate.

TABLE 9

Viscosity (in cP) for Formulations Stored at 60° C.

| Formu-lation | Captisol (mg/mL) | Duration of Storage | | | | | |
|---|---|---|---|---|---|---|---|
| | | 0 days | 1 week | 2 weeks | 1 month | 2 months | 3 months |
| A | 100 | ND | ND | ND | ND | ND | ND |
| B | 200 | ND | ND | ND | ND | ND | ND |
| C | 300 | 4.5-4.2 | 5.09 | 5.0 | 4.7 | 4.90 | 4.50 |
| D | 200 | ND | ND | ND | ND | ND | ND |
| E | 100 | ND | ND | ND | ND | ND | ND |
| F | 200 | ND | ND | ND | ND | ND | ND |
| G | 300 | 4.2 | 4.6 | 4.3 | 4.3 | 4.20 | 4.00 |
| H | 200* | ND | ND | ND | ND | ND | ND |

*Formulation H was prepared with Captisol buffered with sodium phosphate.
** "ND" signifies that viscosity was not determined for the sample.

TABLE 10

Color of Formulations Stored at 60° C.

| Formulation | Duration of Storage | | | | | |
|---|---|---|---|---|---|---|
| | 0 days | 1 week | 2 weeks | 1 month | 2 months | 3 months |
| A | Colorless | Colorless | Very Slightly Yellow | Yellow | Yellow | Dark Yellow |
| B | Colorless | Colorless | Colorless | Slightly Yellow | Pale Yellow | Pale Yellow |
| C | Colorless | Colorless | Colorless | Very Slightly Yellow | Slightly Yellow | Slightly Yellow |
| D | Colorless | Colorless | Colorless | Very Slightly Yellow | Slightly Yellow | Slightly Yellow |
| E | Colorless | Colorless | Colorless | Yellow | Yellow | Yellow |
| F | Colorless | Colorless | Colorless | Slightly Yellow | Pale Yellow | Pale Yellow |
| G | Colorless | Colorless | Colorless | Slightly Yellow | Pale Yellow | Pale Yellow |
| H | Colorless | Colorless | Colorless | Slightly Yellow | Pale Yellow | Pale Yellow |

* All samples were clear solutions without visible precipitate.

TABLE 11

Furosemide Concentration as a Percentage of Theoretical (30 mg/mL) for Formulations Stored at 40° C.

| Formulation | 0 days | 2 months | 3 months | 6 months |
|---|---|---|---|---|
| A | 101.28 | 100.33 | 97.69 | 98.03 |
| B | 100.44 | 101.26 | 99.74 | 98.69 |
| C | 100.45 | 100.26 | 100.32 | 101.28 |
| E | 100.78 | 100.13 | 98.92 | 101.39 |
| F | 100.32 | 100.82 | 99.97 | 100.95 |
| G | 103.43 | 103.76 | 103.69 | 103.87 |
| H | 101.15 | 99.93 | 101.28 | 100.29 |

TABLE 12

Furosemide Area Percentage of Total Chromatogram for Formulations Stored at 40° C.

| Formulation | 0 days | 2 months | 3 months | 6 months |
|---|---|---|---|---|
| A | 100 | 99.64 | 99.26 | 98.43 |
| B | 100 | 99.93 | 99.75 | 99.49 |
| C | 100 | 99.96 | 99.80 | 99.67 |
| E | 100 | 99.94 | 99.67 | 99.34 |
| F | 100 | 99.93 | 99.68 | 99.38 |
| G | 100 | 99.93 | 99.65 | 99.18 |
| H | 100 | 99.94 | 99.67 | 99.29 |

TABLE 13

Peak B Area Percentage of Total Chromatogram for Formulations Stored at 40° C.

| Formulation | 0 days | 2 months | 3 months | 6 months |
|---|---|---|---|---|
| A | 0 | 0.16 | 0.478 | 0.94 |
| B | 0 | 0.07 | 0.151 | 0.351 |
| C | 0 | 0.04 | 0.127 | 0.244 |
| E | 0 | 0.06 | 0.203 | 0.425 |
| F | 0 | 0.07 | 0.199 | 0.395 |
| G | 0 | 0.07 | 0.223 | 0.502 |
| H | 0 | 0.06 | 0.212 | 0.429 |

TABLE 14 pH for Formulations Stored at 40° C.

| Formulation | 0 days | 2 months | 3 months | 6 months |
|---|---|---|---|---|
| A | 7.492 | 7.444 | 7.364 | 7.242 |
| B | 7.545 | 7.523 | 7.485 | 7.494 |
| C | 7.536 | 7.500 | 7.494 | 7.528 |
| E | 7.721 | 7.930 | 7.719 | 7.379 |
| F | 7.258 | 7.625 | 7.544 | 7.246 |
| G | 7.499 | 7.316 | 7.194 | 7.183 |
| H | 7.568 | 7.531 | 7.403 | 7.200 |

TABLE 15

Osmotic Pressure (in mOsm/kg) for Formulations Stored at 40° C.

| Formulation | Captisol (mg/mL) | 0 days | 2 months | 3 months | 6 months |
|---|---|---|---|---|---|
| A | 100 | 343 | 339 | 338 | 345 |
| B | 200 | 733 | 739 | 737 | 717 |
| C | 300 | 1208 | 1455 | 1316 | 1403 |
| E | 100 | 340 | 340 | 342 | 344 |
| F | 200 | 721 | 708 | 740 | 732 |
| G | 300 | 1274 | 1217 | 1244 | 1350 |
| H | 200* | 739 | 750 | 742 | 746 |

*Formulation H was prepared with Captisol buffered with sodium phosphate.

TABLE 16

Viscosity (in cP) for Formulations Stored at 40° C.

| Formulation | Captisol (mg/mL) | 0 days | 2 months | 3 months | 6 months |
|---|---|---|---|---|---|
| A | 100 | ND | ND | ND | ND |
| B | 200 | ND | ND | ND | ND |
| C | 300 | 4.5-4.2 | 5.1 | 4.6 | 4.7 |
| E | 100 | ND | ND | ND | ND |
| F | 200 | ND | ND | ND | ND |
| G | 300 | 4.2 | 4.9 | 4.1 | 4.5 |
| H | 200* | ND | ND | ND | ND |

*Formulation H was prepared with Captisol buffered with sodium phosphate.
** "ND" signifies that viscosity was not determined for the sample.

TABLE 17

Color of Formulations Stored at 40° C.

| Formulation | 0 days | 2 months | 3 months | 6 months |
|---|---|---|---|---|
| A | Colorless | Very Slightly Yellow | Slightly Yellow | Slightly Yellow |
| B | Colorless | Colorless | Colorless | Colorless |
| C | Colorless | Colorless | Colorless | Colorless |
| E | Colorless | Colorless | Very Slightly Yellow | Very Slightly Yellow |
| F | Colorless | Colorless | Colorless | Colorless |
| G | Colorless | Colorless | Colorless | Colorless |
| H | Colorless | Colorless | Colorless | Colorless |

* All samples were clear solutions without visible precipitate.

TABLE 18

Furosemide Concentration as a Percentage of Theoretical (30 mg/mL) for Formulations Stored at 25° C.

| Formulation | 0 days | 6 months |
|---|---|---|
| A | 101.28 | 98.23 |
| B | 100.44 | 98.88 |
| C | 100.45 | 99.18 |
| E | 100.78 | 98.01 |
| F | 100.32 | 99.89 |
| G | 103.43 | 102.79 |
| H | 101.15 | 100.42 |

TABLE 19

Furosemide Area Percentage of Total Chromatogram for Formulations Stored at 25° C.

| Formulation | Duration of Storage | |
|---|---|---|
| | 0 days | 6 months |
| A | 100 | 99.75 |
| B | 100 | 99.88 |
| C | 100 | 99.86 |
| E | 100 | 99.85 |
| F | 100 | 99.82 |
| G | 100 | 99.75 |
| H | 100 | 99.79 |

TABLE 20

Peak B Area Percentage of Total Chromatogram for Formulations Stored at 25° C.

| Formulation | Duration of Storage | |
|---|---|---|
| | 0 days | 6 months |
| A | 0 | 0.162 |
| B | 0 | 0.082 |
| C | 0 | 0.079 |
| E | 0 | 0.101 |
| F | 0 | 0.124 |
| G | 0 | 0.148 |
| H | 0 | 0.137 |

TABLE 21 pH for Formulations Stored at 25° C.

| Formulation | Duration of Storage | |
|---|---|---|
| | 0 days | 6 months |
| A | 7.492 | 7.500 |
| B | 7.545 | 7.608 |
| C | 7.536 | 7.595 |
| E | 7.721 | 7.598 |
| F | 7.258 | 7.591 |
| G | 7.499 | 7.253 |
| H | 7.568 | 7.516 |

TABLE 22

Osmotic Pressure (in mOsm/kg) for Formulations Stored at 25° C.

| Formulation | Captisol (mg/mL) | Duration of Storage | |
|---|---|---|---|
| | | 0 days | 6 months |
| A | 100 | 343 | 349 |
| B | 200 | 733 | 717 |
| C | 300 | 1208 | 1270 |
| E | 100 | 340 | 342 |
| F | 200 | 721 | 735 |
| G | 300 | 1274 | 1363 |
| H | 200* | 739 | 726 |

*Formulation H was prepared with Captisol buffered with sodium phosphate.

TABLE 23

Viscosity (in cP) for Formulations Stored at 25° C.

| Formulation | Captisol (mg/mL) | Duration of Storage | |
|---|---|---|---|
| | | 0 days | 6 months |
| A | 100 | ND | ND |
| B | 200 | ND | ND |
| C | 300 | 4.5-4.2 | 5.3 |
| E | 100 | ND | ND |
| F | 200 | ND | ND |
| G | 300 | 4.2 | 4.2 |
| H | 200* | ND | ND |

*Formulation H was prepared with Captisol buffered with sodium phosphate.
** "ND" signifies that viscosity was not determined for the sample.

TABLE 24

Color of Formulations Stored at 25° C.

| Formulation | Duration of Storage | |
|---|---|---|
| | 0 days | 6 months |
| A | Colorless | Very Slightly Yellow |
| B | Colorless | Colorless |
| C | Colorless | Colorless |
| E | Colorless | Colorless |
| F | Colorless | Colorless |
| G | Colorless | Colorless |
| H | Colorless | Colorless |

* All samples were clear solutions without visible precipitate.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A pharmaceutical composition, comprising:
   from about 15 mg/mL to about 40 mg/mL furosemide, or a pharmaceutically acceptable salt thereof;
   from about 10% to about 40% by weight of a sulfobutyl ether derivative of a β-cyclodextrin;
   about 25 mM of a buffer comprising tris(hydroxymethyl) aminomethane;
   optionally a pH adjusting agent; and
   water;
   wherein the pharmaceutical composition has a pH from about 7.0 to about 8.5.

2. A pharmaceutical composition, comprising:
   about 20 mg/mL to about 40 mg/mL furosemide;
   from about 10% to about 40% by weight of a sulfobutyl ether derivative of β-cyclodextrin;
   about 25 mM of a buffer comprising tris(hydroxymethyl) aminomethane; and
   water;
   wherein the pharmaceutical composition has a pH of from about 7.0 to about 8.5.

3. The pharmaceutical composition of claim 2, wherein the sulfobutyl ether derivative of β-cyclodextrin is captisol.

4. The pharmaceutical composition of claim 2, wherein the pH value of the pharmaceutical composition is from about 7.2 to about 7.6.

5. The pharmaceutical composition of claim 2, wherein the sulfobutyl ether derivative of β-cyclodextrin is present in an amount of from about 20% to about 30% by weight.

6. The pharmaceutical composition of claim 2, wherein the sulfobutyl ether derivative of β-cyclodextrin is present in an amount of about 30% by weight.

7. A pharmaceutical composition, comprising:
   from about 40 mM to about 160 mM of a diuretic selected from the group consisting of 4-chloro-2-((furan-2-ylmethyl)amino)-5-sulfamoylbenzoic acid, a pharmaceutically acceptable salt thereof, and a mixture thereof;
   from about 45 mM to about 190 mM of a sulfobutyl ether derivative of β-cyclodextrin;
   about 25 mM of a buffer comprising tris(hydroxymethyl)aminomethane; and
   water; wherein the pharmaceutical composition has a pH value from about 7.0 to about 8.5.

8. The pharmaceutical composition of claim 7, wherein the pharmaceutical composition comprises from about 120 mM to about 160 mM of a sulfobutyl ether derivative of β-cyclodextrin.

9. The pharmaceutical composition of claim 7, wherein the pharmaceutical composition comprises from about 135 mM to about 145 mM of a sulfobutyl ether derivative of β-cyclodextrin.

10. The pharmaceutical composition of claim 7, wherein the sulfobutyl ether derivative of β-cyclodextrin is sulfobutyl ether beta-cyclodextrin sodium.

11. The pharmaceutical composition of claim 8, wherein the pharmaceutical composition comprises from about 80 mM to about 100 mM of the diuretic.

12. The pharmaceutical composition of claim 9, wherein the pharmaceutical composition comprises about 91 mM of the diuretic.

13. The pharmaceutical composition of claim 7, wherein the pharmaceutical composition has a pH of from about 7.0 to about 8.0.

14. The pharmaceutical composition of claim 11, wherein the pharmaceutical composition has a pH of about 7.4.

15. The pharmaceutical composition of claim 7, wherein the pharmaceutical composition contains at least 50% (w/w) water.

16. The pharmaceutical composition of claim 7, wherein less than 1% of the diuretic degrades upon storage of the pharmaceutical composition at 40° C. for 29 days.

17. The pharmaceutical composition of claim 7, wherein less than 1% of the diuretic degrades upon storage of the pharmaceutical composition at 25° C. for 24 months.

18. The pharmaceutical composition of claim 7, wherein the pharmaceutical composition comprises:
   from 40 mM to 160 mM of a diuretic selected from the group consisting of 4-chloro-2-((furan-2-ylmethyl)amino)-5-sulfamoylbenzoic acid, a pharmaceutically acceptable salt thereof, and a mixture thereof;
   from about 45 mM to about 190 mM of a sulfobutyl ether derivative of β-cyclodextrin;
   about 25 mM of a buffer comprising tris(hydroxymethyl)aminomethane;
   optionally a pH adjusting agent; and
   water;
   wherein the pharmaceutical composition has a pH value from about 7.0 to about 8.5.

19. The pharmaceutical composition of claim 18, wherein the sulfobutyl ether derivative of β-cyclodextrin is present at a concentration of from about 135 mM to about 145 mM in the pharmaceutical composition.

20. The pharmaceutical composition of claim 18, wherein the sulfobutyl ether derivative of β-cyclodextrin is sulfobutyl ether beta-cyclodextrin sodium.

21. The pharmaceutical composition of claim 19, wherein the sulfobutyl ether derivative of β-cyclodextrin is sulfobutyl ether beta-cyclodextrin sodium.

22. The pharmaceutical composition of claim 18, wherein the diuretic is present at a concentration of from about 80 mM to about 100 mM in the pharmaceutical composition.

23. The pharmaceutical composition of claim 21, wherein the diuretic is present at a concentration of from about 80 mM to about 100 mM in the pharmaceutical composition.

24. The pharmaceutical composition of claim 18, wherein the diuretic is present at a concentration of about 91 mM in the pharmaceutical composition.

25. The pharmaceutical composition of claim 21, wherein the diuretic is present at a concentration of about 91 mM in the pharmaceutical composition.

26. The pharmaceutical composition of claim 18, wherein the pharmaceutical composition has a pH of about 7.4.

27. The pharmaceutical composition of claim 25, wherein the pharmaceutical composition has a pH of about 7.4.

28. A method of treating a condition selected from edema, heart failure, kidney disease, or liver disease, or symptoms thereof, comprising administering to a patient in need thereof a therapeutically effective amount of a pharmaceutical composition of claim 2 to treat the condition.

* * * * *